United States Patent [19]

Fragale et al.

[11] Patent Number: 4,599,453
[45] Date of Patent: Jul. 8, 1986

[54] PROCESS FOR THE SINGLE-STAGE PRODUCTION OF HIGHER ALIPHATIC KETONES

[75] Inventors: Carlo Fragale; Michele Gargano; Michele Rossi, all of Bari, Italy

[73] Assignee: Consiglio Nazionale Delle Ricerche, Rome, Italy

[21] Appl. No.: 705,010

[22] Filed: Feb. 25, 1985

[51] Int. Cl.$^4$ ............................................. C07C 45/49
[52] U.S. Cl. .................................. 568/387; 568/879; 568/881
[58] Field of Search ............... 568/388, 387, 396, 389, 568/386, 881, 879; 423/656

[56] References Cited

U.S. PATENT DOCUMENTS

| | | | |
|---|---|---|---|
| 2,077,421 | 4/1937 | Lazier | 568/396 |
| 2,130,592 | 9/1938 | McAllister | 568/396 |
| 2,419,142 | 4/1947 | Ipatieff et al. | 568/388 |
| 2,825,743 | 3/1958 | MacLean et al. | 568/396 |
| 3,615,217 | 10/1971 | O'Brian et al. | 423/656 |
| 3,631,822 | 1/1971 | Schmitt et al. | 568/396 |
| 3,899,577 | 8/1975 | Sugier | 423/656 |
| 4,049,571 | 9/1977 | Nissen et al. | 568/396 |
| 4,126,581 | 11/1978 | Sugier et al. | 423/565 |
| 4,177,252 | 12/1979 | Chinchen | 423/656 |
| 4,289,911 | 9/1981 | Isogai et al. | 568/396 |

*Primary Examiner*—James H. Reamer
*Attorney, Agent, or Firm*—Stevens, Davis, Miller & Mosher

[57] ABSTRACT

A process for the single-stage production in the liquid or gaseous phase, of higher aliphatic ketones starting from ketones of lower molecular weight, characterized in that the starting ketones are reacted with carbon monoxide in the presence of a catalyst in the form of cooper supported on a metal oxide.

The catalyst is prepared by depositing on the metal oxide the product obtained from hydrolyzing a cuprammonium solution, then calcining the solid system obtained in air and reducing the calcined product by means of hydrogen.

9 Claims, No Drawings

PROCESS FOR THE SINGLE-STAGE PRODUCTION OF HIGHER ALIPHATIC KETONES

This invention relates to a new process for the production of higher aliphatic ketones from ketones of lower molecular weight.

Processes for the production, for example, of methylisobutylketone from acetone are well known.

This production is effected in three stages in the conventional process:

the first stage consists of the aldol condensation of the acetone (I), catalysed by a base, to produce diacetone alcohol (II):

$$2CH_3-CO-CH_3 \underset{}{\overset{base}{\rightleftarrows}} \underset{I}{\phantom{XX}} \underset{CH_3}{\underset{|}{CH_3-COH-CH_2-CO-CH_3}} \phantom{XX}_{II}$$

the second stage consists of the removal of $H_2O$, catalysed in the liquid phase by $H_2SO_4$ or $H_3PO_4$, at a temperature of about 100° C. to obtain mesityl oxide (III):

$$\underset{CH_3}{\underset{|}{CH_3-COH-CH_2-CO-CH_3}} \overset{H_2SO_4}{\rightleftarrows} \underset{CH_3}{\underset{|}{CH_3-C=CH-CO-CH_3}} + H_2O$$
$$III$$

the third stage consists of the hydrogenation of the mesityl oxide at a temperature of 150°–200° C. and a pressure of 3–10 bars in the presence of copper or nickel catalysts, to produce methylisobutylketone (IV):

$$\underset{CH_3}{\underset{|}{CH_3-C=CH-CO-CH_3}} \overset{H_2}{\rightleftarrows} \underset{CH_3}{\underset{|}{CH_3-CH-CH_2-CO-CH_3}}$$
$$IV$$

In order to simplify this process, various methods have been proposed which attempt to reduce the three stages to a single stage by operating in the presence of suitably prepared catalysts (for example French Pat. No. 2,056,450; Japanese Pat. 74/06,290; British Pat. No. 1,269,891; French Pat. No. 2,064,778).

The catalytic systems used in these single-stage processes generally consist of one or more transition metal (Ru, Rh, Ir, Ni, Pd, Pt, Cu, Cr etc.) dispersed on matrices able to catalyse the condensation of acetone to α, β unsaturated ketones (CaO, MgO, $Al_2O_3$, $SiO_2$, $TiO_2$, ZnO etc.).

The reduction is conducted using gaseous hydrogen at a pressure of between 1 and 50 bars, and operating at a temperature of between 100° and 350° C.

The results of the reaction in terms of selectivity vary considerably with the degree of acetone conversion, the reaction conditions and the catalytic system used. The best results have been obtained with a Pd-Zr-P catalytic system.

We have now discovered a new process for the production of higher aliphatic ketones from ketones of lower molecular weight, operating in a single stage.

The process according to the present invention is characterised in that the starting ketone is reacted in the presence of CO over a catalyst in the form of copper supported on a metal oxide.

The process according to the present invention is further characterised in that the catalyst is prepared by precipitating, by hydrolysis, a cuprammonium complex on an oxide such as $Al_2O_3$, $SiO_2$, $TiO_2$, $ZrO_2$, MgO, ZnO, $Cr_2O_3$ etc., followed by calcining in air and reduction in a hydrogen stream.

A further characteristic of the process according to the present invention is that the reaction can be conducted either in the liquid phase or in the gaseous phase.

A possible theoretical interpretation of the phenomens which occur in the process of the present invention can be represented by the following scheme, which relates to the preparation of metylisobutylketone starting from acetone.

$$2CH_3-CO-CH_3 \rightleftarrows \underset{CH_3}{\underset{|}{CH_3-COH-CH_2-CO-CH_2}} \quad (1)$$

$$\underset{}{CH_3-COH-CH_2-CO-CH_3} \rightleftarrows \underset{CH_3}{\underset{|}{CH_3-C=CH-CO-CH_3}} + H_2O \quad (2)$$

$$H_2O + CO \rightleftarrows H_2 + CO_2 \quad (3)$$

$$\underset{CH_3}{\underset{|}{CH_3-C=CH-CO-CH_3}} + H_2 \rightleftarrows \underset{CH_3}{\underset{|}{CH_3-CH-CH_2-CO-CH_3}} \quad (4)$$

Overall, the process can be represented by the following reaction:

$$2CH_3-CO-CH_3 + CO \rightleftarrows \underset{CH_3}{\underset{|}{CH_3-CH-CH_2-CO-CH_3}} + CO_2 \quad (5)$$
$$IV$$

The methylisobutylketone (IV) can further react to give ketones of higher molecular weight, for example it can react in accordance with the following reactions:

$$IV + CH_3-CO-CH_3 + CO \longrightarrow \quad (6)$$

$$\underset{CH_3}{\underset{|}{CH_3-CH-CH_2-CO-CH_2-CH-CH_3}}\underset{CH_3}{\underset{|}{}}$$
$$V$$

$$IV + 2CH_3-CO-CH_3 + 2CO \longrightarrow \quad (7)$$

-continued

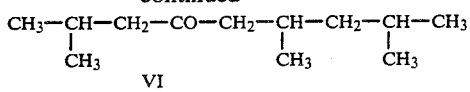

In this manner, diisobutylketone (V) and 2,4,8-trimethylnonan-6-one (VI) are obtained.

According to the aforesaid scheme, the hydrogen necessary for reducing the α, β unsaturated ketones is produced in-situ by the water gas conversion reaction catalysed by the copper dispersed on the catalyst surface (reaction 3).

An advantage of the process according to the present invention is therefore the fact that the water produced in condensing the acetone to mesityl oxide (reactions 1 and 2) is completely consumed in producing the hydrogen necessary for reducing the unsaturated ketone (reaction 4) and this tends to further increase the degree of advancement of reaction 2.

The catalyst for use in the process according to the present invention is preferably prepared by the following method, although other catalyst preparation methods can be used within the scope of the invention.

An aqueous solution of a cuprammonium complex is prepared starting from $Cu(NO_3)_2.3H_2O$, $CuSO_4.10H_2O$, $Cu(ClO_4)_2.6H_2O$ or other copper salts, the solution having a Cu content of between 2 and 20 g/l and preferably between 12 and 15 g/l, and being stabilised with a slight excess of ammonia.

$Al_2O_3$ is added to this solution in a quantity such as to obtain a weight ratio of Cu to $Al_2O_3$ of between 0.015 and 0.15, and preferably between 0.085 and 0.11, said $Al_2O_3$ having the following characteristics: crystalline structure type γ, particle size distribution between 50 and 150 μm (100-290 mesh ASTM), specific surface preferably between 150 and 200 m$^2$/g.

The suspension is diluted with distilled water until the copper concentration lies between 0.2 and 6 g/l, and preferably between 0.9 and 1.2 g/l.

During the dilution, the suspension is kept under agitation (500 r.p.m.) at a temperature preferably of between 10° and 30° C.

By virtue of the dilution, the cuprammonium complex hydrolyses, and the hydrolysis product is deposited in a finely dispersed form on the surface of the $Al_2O_3$ particles.

The solid is then filtered, after which it is washed three times with between 30 and 50 ml/g of distilled water, the product then being calcined in air at a temperature of between 250° and 400° C. for a time of between 1 and 10 hours, and preferably for a time of between 3 and 4 hours. The calcined product is then reduced in a hydrogen stream by forming the catalyst into a fixed bed and passing the hydrogen over it at a flow rate of between 1 and 100 ml/min. The reduction temperature is kept constant at between 150° and 350° C.

The reaction time is between 5 and 90 minutes, and preferably between 10 and 20 minutes.

The catalyst thus obtained consists of Cu supported on $Al_2O_3$. The Cu content of the catalyst is between 5 and 10%, the particle size distribution is between 50 and 100 μm (100-290 mesh ASTM), and the specific surface is between 200 and 250 m$^2$/g.

Other oxides can be used instead of the $Al_2O_3$ for the catalyst support, such as $SiO_2$, $TiO_2$, $ZrO_2$, MgO or ZnO.

The reaction for producing higher ketones from acetone in the liquid phase is conducted in the following manner.

The acetone and catalyst are fed into a metal reactor in an acetone/Cu molar ratio of between 50 and 500 and preferably between 90 and 150. Carbon monoxide is then fed in until a pressure of between 0.5 and 80 bars and preferably between 15 and 40 bars is reached. The reactor is heated to a temperature of between 120° and 220° C. and preferably between 140° and 200° C. The reaction is conducted for a time of between 0.25 and 15 hours and preferably between 0.5 and 4 hours.

If the required product is methylisobutylketone, it is convenient to operate at the lower limits of the reaction pressure, temperature and time ranges, compatible with a reasonable level of acetone conversion, for example around 50%. At the higher limits of these ranges substantial quantities of diisobutylketone form at the expense of the methylisobutylketone.

The reaction for producing higher ketones in the liquid phase from ketones other than acetone, for example from butan-2-one, from methylisobutylketone etc., is conducted in the same manner as described for acetone, but with the difference that the reaction time has to be increased, preferably up to 14 hours.

When operating with butan-2-one, with a conversion exceeding 65%, 3-methylheptan-5-one can be obtained with a selectivity exceeding 90%. When operating with methylisobutylketone, with a conversion exceeding 85%, 2,4,8-trimethylnonane-6-one can be obtained with a selectivity exceeding 90%.

The process according to the present invention can also be conducted in the gaseous phase. In this case, the catalyst is fed into a tubular reactor which is heated to a temperature of between 120° and 220° C. and preferably between 140° and 180° C. A gaseous stream of carbon monoxide and ketone, preferably in a molar ratio close to 2/1, is passed through the reactor at a pressure slightly greater than atmospheric pressure.

The results obtained by operating in the gaseous phase are analogous to those obtained by operating in the liquid phase.

The following examples are given in order to illustrate the operational method and characteristics of the process according to the present invention.

EXAMPLE 1

20 g of γ$Al_2O_3$ of particle size distribution between 50 and 150 μm (100-290 mesh ASTM) and specific surface 175 m$^2$/g were added to a solution containing 8 g of cuprammonium complex prepared from $Cu(NO_3)_2.3H_2O$ in 150 ml of water, stabilised by adding 3 ml of concentrated ammonia.

The mixture thus obtained was diluted with 2 liters of distilled water st a temperature of 25° C., maintaining energetic agitation (500 r.p.m.) during the dilution, so as to cause hydrolysis of the cuprammonium complex and deposition of the hydrolysis product in finely dispersed form on the surface of the $Al_2O_3$ granules.

The solid product was separated by filtration, washed with three portions of distilled water each of 1 liter volume, calcined in air at 350° C. for 180 minutes, and finally reduced in a hydrogen stream at 270° C. for 15 minutes by forming it into a layer having a thickness of 1 cm and passing hydrogen over it at a throughput of 20 ml/min.

A catalyst was obtained constituted by Cu supported on $Al_2O_3$, containing 4.5% of Cu and in the form of particles of size distribution 50-150 μm (100-290 mesh ASTM), and with a specific surface of 260 m²/g.

EXAMPLE 2

1 g of catalyst prepared as described in Example 1 and 5 ml of acetone (acetone/Cu molar ratio 96) were placed in a 100 ml AISI 316 stainless steel reactor provided with a cock, pressure gauge and mechanical agitator.

Carbon monoxide was fed through the reactor cock until a pressure of 40 bars was reached in the reactor. The carbon monoxide used had the following analytical characteristics: % $H_2$=1.0, %CO=99.0.

The reaction temperature was rapidly raised to 180° C. by means of a temperature-controlled oven, and as soon as heating started the reactor was put under vigorous agitation.

The reaction time in the test of this example was 0.5 hours. At the end of the test, the reactor was cooled rapidly by a stream of water, and after evacuating the gaseous atmosphere the reactor was opened in order to separate the catalyst from the reaction product by filtration.

When analysed by gas chromatography, the reaction product was found to consist of a high percentage of methylisobutylketone, and smaller percentages of diisobutylketone and other compounds, as shown in Table 1 accompanying Examples 3 to 5.

EXAMPLES 3 TO 5

Examples 3 to 5 were conducted in the same manner as Example 2, but with the difference that the reaction times were 1, 2 and 4 hours respectively.

The products obtained were analysed by gas chromatography, and the results are shown in the following Table 1:

TABLE 1

| Ex. No. | Reaction time (hours) | Acetone convers. % | \multicolumn{8}{c}{Products % by weight} |
|---|---|---|---|---|---|---|---|---|---|---|
| | | | IPA | MOX | MIBK | MIBC | DIBK | DIBC | C12 | Others |
| 2 | 0.5 | 36.7 | 7.8 | 7.9 | 75.9 | — | 8.4 | — | — | 0.2 |
| 3 | 1 | 77.3 | 2.1 | 0.4 | 74.6 | 2.3 | 18.8 | 0.4 | 1.5 | 0.7 |
| 4 | 2 | 88.8 | 1.1 | 0.1 | 69.1 | 0.9 | 25.9 | 0.2 | 2.7 | 1.5 |
| 5 | 4 | 96.0 | 0.8 | — | 59.8 | 4.0 | 29.7 | 1.1 | 4.6 | 2.8 | in which the symbols have the following meanings: IPA=isopropanol; MOX=mesityl oxide; MIBK=methylisobutylketone; MIBC=methylisobutylcarbinol; DIBK=diisobutylketone; DIBC=diisobutylcarbinol.

EXAMPLES 6 TO 8

These examples were conducted in the same operating manner as Example 2, but varying the reaction parameters, namely carbon monoxide pressure, reaction temperature and reaction time, as shown in the following Table 2:

TABLE 2

| Ex. No. | CO pressure (bars) | Temperature (°C.) | Reaction time (hours) |
|---|---|---|---|
| 6 | 40 | 140 | 4 |
| 7 | 40 | 220 | 1 |
| 8 | 15 | 180 | 4 |

The products obtained were analysed by gas chromatography, and the results are shown in the following Table 3:

TABLE 3

| Ex. No. | Acetone conversion (%) | IPA | MOX | MIBK | MIBC | DIBK | DIBC | C12 | Others |
|---|---|---|---|---|---|---|---|---|---|
| 6 | 52.4 | 6.2 | 5.4 | 83.1 | — | 5.3 | — | — | 0.5 |
| 7 | 92.6 | 1.6 | 0.1 | 58.6 | 4.6 | 29.0 | 1.5 | 4.9 | 2.0 |
| 8 | 63.9 | 0.7 | 6.7 | 78.5 | — | 13.6 | — | 0.5 | 3.4 | in which the symbols have the meanings associated with Table 1.

EXAMPLE 9 (COMPARISON)

This example was conducted in the same operating manner as Example 2, but with a reaction time of 4 hours and using $Al_2O_3$ as catalyst, without the Cu.

Gas chromatography analysis of the reaction products showed an acetone conversion of 17.6%, the product consisting of 86.5% mesityl oxide and 15.5% of unidentified components.

EXAMPLE 10 (COMPARISON)

The procedure of Example 2 was followed, but with a reaction time of 4 hours and using nitrogen instead of carbon monoxide. The acetone conversion was 16.2%, and the product consisted of 89% mesityl oxide and 11% of unidentified compounds.

EXAMPLE 11

In this example, in contrast to the preceding examples, the reaction was conducted in the gaseous phase in the following manner. 10 g of catalyst prepared as described in Example 1 were placed in a horizontal reactor constituted by a glass tube of 1 cm inner diameter. The catalyst was disposed in a layer of height 10 mm.

The temperature was raised to 180° C. by means of a tubular oven, and a gaseous stream of carbon monoxide and acetone in a molar ratio of 2/1 was passed through the reactor. The feed throughput was 0.3 millimoles of acetone per minute, and the pressure inside the reactor was maintained at 1.3 bars.

After an initial period of 3 hours, the reaction products were collected by means of a trap kept at a temperature of −15° C.

Gas chromatography analysis showed an acetone conversion of 97%, the product consisting of 51% methylisobutylketone, 34% diisobutylketone, 6% 2,4,8-trimethylnonan-6-one, 3.5% mesityl oxide, and 4.5% of unidentified products.

EXAMPLE 12

This example was conducted in the manner of Example 2, but with a reaction time of 3 hours and using butan-2-one instead of acetone.

Gas chromatography analysis of the reaction mixture showed a butan-2-one conversion of 68.1%, the mixture composition being 94.3% 5-methylheptan-3-one, 3.6% butan-2-ol, and 2.1% of other unidentified compounds.

EXAMPLE 13

This example was conducted in the manner of Example 2, but with a reaction time of 14 hours and using methylisobutylketone instead of acetone.

Gas chromatography analysis of the reaction mixture showed a methylisobutyl conversion of 86.1%, the reaction mixture consisting of 93% 2,4,8-trimethylnonan-6-one, 4.2% metylisobutylcarbinol, and 2.7% of other unidentified compounds.

We claim:

1. A single stage process for the production of a higher aliphatic ketone starting from a ketone of lower molecular weight, which comprises reacting a ketone of lower molecular weight with carbon monoxide at temperatures between 120° C. and 220° C. at a carbon monoxide partial pressure between 0.5 and 80 bars and in the presence of a catalyst consisting of copper supported on aluminum oxide, said catalyst being obtained by hydrolyzing an aqueous solution of a cuproammonium complex containing aluminum oxide to form a copper-containing precipitate on the aluminum oxide, calcining said copper-containing precipitate on aluminum oxide, and then heating the said calcined copper-containing precipitate on aluminum oxide with hydrogen at a temperature between 100° and 350° C.

2. A process as claimed in claim 1, wherein the copper-containing precipitate is calcined in air at a temperature between 150° C. and 400° C. for a time between 1 and 10 hours.

3. A process as claimed in claim 2, wherein the copper-containing precipitate is calcined in air at a temperature between 320° C. and 350° C. for a time between 3 and 4 hours.

4. A process as claimed in claim 1, wherein the calcined precipitate is heated with hydrogen at a temperature of between 100° C. and 350° C. for a time between 5 and 90 minutes.

5. A process as claimed in claim 4, wherein the calcined precipitate is heated with hydrogen at a temperature between 250° C. and 280° C. for a time between 10 and 20 minutes.

6. A process as claimed in claim 1, wherein the lower molecular weight ketone is reacted with carbon monoxide in a liquid phase.

7. A process as claimed in claim 1, wherein the lower molecular weight ketone is reacted with carbon monoxide in a gaseous phase.

8. A process as claimed in claim 7, wherein the catalyst is fed into a tubular reactor heated to a temperature of between 120° C. and 220° C., while passing through the reactor a gaseous stream comprising carbon monoxide and the lower molecular weight ketone in a molar ratio of between 1/1 and 4/1 at a pressure slightly exceeding atmospheric pressure.

9. A process as claimed in claim 8, wherein the catalyst is fed into a tubular reactor heated to a temperature between 140° C. and 180° C., while passing through the reactor a gaseous stream comprising carbon monoxide and the lower molecular weight ketone in a molar ratio of about 2/1 at a pressure slightly exceeding atmospheric pressure.

* * * * *